United States Patent [19]

Paciorek et al.

[11] 4,194,983

[45] Mar. 25, 1980

[54] PERFLUORINATED POLYALKYLETHER BASED LUBRICANT COMPOSITION

[75] Inventors: Kazimiera J. L. Paciorek, Corona Del Mar; Reinhold H. Kratzer, Irvine; Jacquelyn Kaufman, Costa Mesa; Thomas I. Ito; James H. Nakahara, both of Fountain Valley, all of Calif.

[73] Assignee: The United States of America as represented by the Secretary of the Air Force, Washington, D.C.

[21] Appl. No.: 9,728

[22] Filed: Feb. 6, 1979

[51] Int. Cl.² ................................................ C10M 1/10
[52] U.S. Cl. ................................ 252/49.9; 252/389 A
[58] Field of Search ............................ 252/49.9, 389 A

[56] References Cited

U.S. PATENT DOCUMENTS

| 3,136,727 | 6/1964 | Nichols | 252/49.9 |
| 3,242,218 | 3/1966 | Miller | 252/54 X |
| 3,306,854 | 2/1967 | Gumprecht | 252/49.9 |
| 3,313,731 | 4/1967 | Dolle, Jr. et al. | 252/49.9 X |
| 3,316,330 | 4/1967 | Nichols | 252/49.9 X |
| 3,393,151 | 7/1968 | Dolle, Jr. et al. | 252/49.9 |
| 3,410,809 | 11/1968 | Johns | 252/49.9 X |
| 4,043,926 | 8/1977 | Snyder, Jr. et al. | 252/49.9 |

FOREIGN PATENT DOCUMENTS 1350806 of 1974 United Kingdom .

*Primary Examiner*—Andrew Metz
*Attorney, Agent, or Firm*—Joseph E. Rusz; Cedric H. Kuhn

[57] ABSTRACT

A lubricant composition comprising a perfluorinated polyalkylether base fluid and a minor amount of a diphospha-s-triazine in which the two phosphorus atoms are substituted by aromatic groups and the carbon atom is substituted by a perfluoroalkyl or perfluoroalkylether moiety.

10 Claims, No Drawings

PERFLUORINATED POLYALKYLETHER BASED LUBRICANT COMPOSITION

RIGHTS OF THE GOVERNMENT

The invention described herein may be manufactured and used by or for the Government of the United States for all governmental purposes without the payment of any royalty.

FIELD OF THE INVENTION

This invention relates to lubricant compositions based upon perfluorinated polyalkylether base fluids and containing a diphospha-s-triazine antioxidant-anticorrosion additive.

BACKGROUND OF THE INVENTION

Because of their thermal stability, perfluorinated polyalkylether fluids possess a great potential for use as engine oils, hydraulic fluids and greases. However, a serious drawback in their use results from the fact that metals, e.g., certain ones present in aircraft engine components, are corroded at temperatures above 550° F. in an oxidative environment. For example, when the fluids are employed as lubricants for mechanical components composed of mild steels, corrosion has occurred at temperatures of from 550° to 600° F.

In U.S. Pat. No. 4,043,926, C. E. Snyder, Jr., and C. Tamborski disclose that perfluoroalkylether substituted aryl phosphines are effective as anticorrosion additives for perfluorinated polyalkylether fluids. It would be desirable to provide alternative additive materials that would be capable of inhibiting the tendency of such fluids to corrode metals at elevated temperatures.

It is a principal object of this invention, therefore, to provide an improved lubricant composition which contains, as the base fluid, a perfluorinated polyalkylether.

Another object of the invention is to provide a lubricant composition that is substantially non-corrosive to ferrous and titanium alloys.

Other objects and advantages of the invention will become apparent to those skilled in the art upon consideration of the accompanying disclosure.

SUMMARY OF THE INVENTION

The present invention resides in a lubricant composition comprising a perfluorinated polyalkylether base fluid and a corrosion inhibiting amount of a diphospha-s-triazine in which the two phosphorus atoms are substituted by aromatic groups and the carbon atom is substituted by a perfluoroalkyl or perfluoroalkylether moiety. The lubricant composition functions as a noncorrosive, stable material suitable for long term applications over a wide temperature range in an oxidative environment.

In general, any suitable perfluorinated polyalkylether can be used as a base fluid in formulating the lubricant of this invention. It is often preferred to employ a material having the following formula:

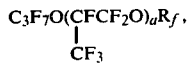

where $R_f$ is a perfluoroalkyl group containing 2 or 3 carbon atoms and a is an integer ranging from 5 to 50, inclusive, preferably from about 10 to 40, inclusive. The value of a is usually such that the compound has a molecular weight ranging from about 2000 to 7000 and a kinematic viscosity ranging from about 15 to 500 centistokes at 100° F. Perfluorinated polyalkylethers corresponding to the above formula are commercially available compounds that are described in the literature. For a detailed description of a method for preparing the compounds, reference may be made to U.S. Pat. No. 3,242,218.

The diphospha-s-triazines used as corrosion inhibitors in the lubricant composition of this invention have the following formula:

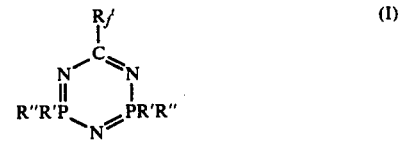

wherein $R_f'$ is a perfluoroalkyl or perfluoroalkylether group and R' and R" are the same or different aryl groups. Examples of the $R_f'$ substituent include groups having formula $C_nF_{2n+1}$, where n is an integer from 1 to 10, inclusive, $CF_3(OCF_2CF_2)_xOCF_2$, $C_2F_5(OCF_2CF_2)_xOCF_2$, and $C_3F_7[OCF(CF_3)CF_2]_x\text{-}OCF(CF_3)$, where x is zero or an integer from 1 to 20, inclusive, preferably an integer from 1 to 4, inclusive. Examples of the R' and R" groups include $C_6H_5$, $R\text{—}C_6H_4$, where R is an aromatic, alkyl, perfluoroalkyl or perfluoroalkylether moiety, and a perfluoroaryl, such as $C_6F_5$ and $R_f\text{—}C_6H_4$, where $R_f$ is a perfluoroalkyl or perfluoroalkylether group.

The process employed in synthesizing the diphospha-s-triazines can be represented by the following equation:

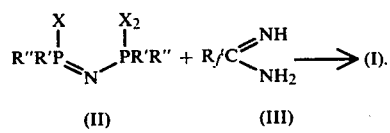

In the above equation, $R_f'$, R' and R" are as defined above while X is chlorine or bromine. As shown by the equation, an imido-tetraaryl-diphosphinic acid trihalide (II) is reacted with perfluoroalkyl or perfluoroalkylether amidine (III), giving the diphospha-s-triazine (I). During the reaction, which is conducted at a temperature ranging from about 95° to 155° C., hydrogen halide is evolved. The reaction is carried out under an inert gas, such as nitrogen, helium or argon. In general, equimolar amounts of the reactants are utilized although it is often preferred to employ a small excess of the diphosphinic acid trihalide (II). For example, the mole ratio of compound II to compound III can vary from about 1 to 1.5 to 1.

The materials used in preparing the triazine products are known compounds that are described in the literature. For example, imido-tetraphenyl-diphosphinic acid trichloride is described by E. Fluck et al in Chem. Ber., 96, 3091 (1963). Perfluoro-n-heptylamidine is described by H. C. Brown in J. Polymer Sci., 44, 9 (1960) and by D. R. Husted in U.S. Pat. No. 2,676,985 (1954). Perfluoroalkylether amidines are described by P. D. Schuman et al in British Patent 1,350,806 (1974).

A more detailed description of the synthesis of the diphospha-s-triazines is contained in our copending U.S. patent application Ser. No. 010,092, filed on Feb. 7, 1979. The disclosure of that application is incorporated herein by reference.

In formulating the lubricant of this invention, a corrosion inhibiting amount of the triazine compound is mixed with the perfluoriunated polyalkylether base fluid. The amount of the triazine compound used is usually in the range of about 0.05 to 5 weight percent, preferably 0.5 to 2 weight percent, based upon the weight of the base fluid.

A more complete understanding of the invention can be obtained by referring to the following illustrative examples which are not intended, however, to be unduly limitative of the invention.

EXAMPLE I

A series of runs was conducted for the purpose of demonstrating the effectiveness of a diphospha-s-triazine of this invention as an antioxidant-anticorrosion additive for a perfluorinated polyalkylether base fluid. A lubricant composition was formulated by mixing (1) a base fluid having the following formula:

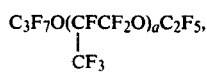

$$C_3F_7O(CFCF_2O)_aC_2F_5,$$
$$|$$
$$CF_3$$

where a is an integer having a value such that the fluid has a kinematic viscosity of 258.4 at 100° F. with (2) 1 weight percent, based upon the weight of the base fluid, of a diphospha-s-triazine having the following formula:

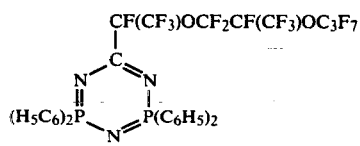

The base fluid used as Krytox 143AC fluid, a product of E. I. duPont de Nemours and Company, Wilmington, Del.

The lubricant composition prepared as described above and the fluid in the absence of the triazine additive were exposed to oxygen at 600° F. over a 24-hour period. The presence of the additive decreased oxygen consumption to zero and volatile products formation by a factor of 60 as compared to the fluid containing no additive.

A run was carried out in which a coupon of M-50 tool steel coupon was suspended in a sealed glass tube containing the lubricant composition prepared as described above. The run was conducted in pure oxygen at 600° F. for a period of 24 hours. A control run was conducted in the same manner except that the fluid did not contain the triazine additive. At the conclusion of the runs, the oxygen was measured and the products were collected and measured. The results obtained are summarized below in the table.

TABLE

| Fluid Used,g | Additive wt % | Oxygen Consumed | | | Total Products Formed | |
|---|---|---|---|---|---|---|
| | | Total, mg | Percent[1] | mg/g[2] | mg | mg/g[3] |
| 12.13 | none | 70.8 | 24.6 | 5.84 | 576.7 | 47.54 |
| 16.36 | 1.0 | 0.0 | 0.0 | 0.0 | 12.7 | 0.78 |

[1]Percent of oxygen available.
[2]Oxygen consumed in mg/g fluid employed.
[3]Products formed in mg/g fluid employed.

The M-50 coupon surface in the presence of the additive appeared unchanged. In the absence of any additive, under otherwise identical conditions, the surface of the coupon was covered with deeply colored, irregular deposits.

EXAMPLE II

Runs are carried out in which lubricant compositions of this invention are formulated by mixing the fluid described in Example I with 0.75 and 2.0 weight percent 1,3-bis(diphenylphospha)-5-[C_3F_7O[CF(CF_3)C-F_2O]_2CF(CF_3)]-2,4,6-triazine. The compositions are subjected to the tests described in Example I and the results of the tests are substantially the same as in Example I.

As seen from the foregoing, the lubricant composition of this invention has little, if any, corrosive effect upon metal alloys. Also, there was substantially no degradation of the base fluid itself at elevated temperatures. Because of these outstanding properties, the lubricants can be employed in applications requiring extreme temperature conditions. Examples of uses for the lubricants include gas turbine engine lubricants, nonflammable hydraulic fluids, greases compatible with liquid oxygen, and liquid coolants and general purpose lubricants.

As will be evident to those skilled in the art, modification of the present invention can be made in view of the foregoing disclosure without departing from the spirit and scope of the invention.

We claim:

1. A lubricant composition comprising (1) a perfluorinated polyalkylether base fluid and (2) a corrosion inhibiting amount of a diphospha-s-triazine having the following formula:

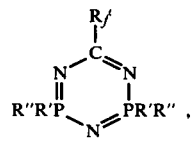

wherein $R_f'$ is a perfluoroalkyl or perfluoroalkylether group and R' and R" are the same or different aryl groups.

2. The lubricant composition of claim 1 in which the amount of the diphospha-s-triazine ranges from about 0.05 to 5 weight percent, based upon the weight of the base fluid.

3. The lubricant composition of claim 1 in which the amount of the diphospha-s-triazine ranges from about 0.5 to 2 weight percent, based upon the weight of the base fluid.

4. The lubricant composition of claim 1 in which the perfluorinated polyalkylether base fluid is a compound having the following formula:

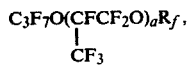

where $R_f$ is a perfluoroalkyl group containing 2 or 3 carbon atoms and a is an integer ranging from 5 to 50, inclusive.

5. The lubricant composition of claim 1 in which the $R_f$ group of the diphospha-s-triazine is a group hvaing the formula $C_nF_{2n+1}$, where n is an integer from 1 to 10, inclusive, $CF_3(OCF_2-CF_2)_xOCF_2$, $C_2F_5(OCF_2CF_2)_xOCF_2$, or $C_3F_7[OCF(CF_3)CF_2]_xOCF(CF_3)$, where x is zero or an integer from 1 to 20, inclusive, and R' and R" are individually selected from the group consisting of $C_6H_5$, $R-C_6H_4$, where R is an aromatic, alkyl, perfluoroalkyl or perfluoroalkylether moiety, $C_6F_5$, and $R_f-C_6H_4$, where $R_f$ is a perfluoroalkyl or perfluoroalkylether group.

6. The lubricant composition of claim 5 in which the diphospha-s-triazine has the following formula:

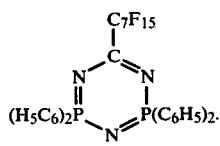

7. The lubricant composition of claim 5 in which the diphospha-s-triazine has the following formula:

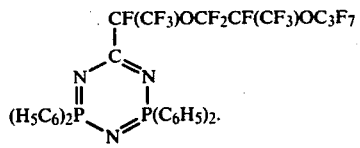

8. The lubricant composition of claim 5 in which the diphospha-s-triazine has the following formula:

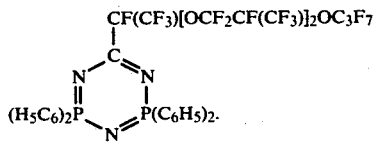

9. The lubricant composition of claim 5 in which the diphospha-s-triazine has the following formula:

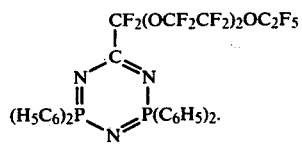

10. The lubricant composition of claim 5 in which the diphospha-s-triazine has the following formula:

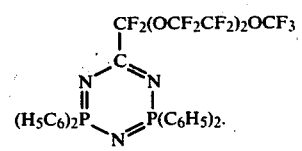

* * * * *